United States Patent [19]

Yamatsu et al.

[11] 4,325,974

[45] Apr. 20, 1982

[54] β, γ-DIHYDROPOLYPRENYL ALCOHOL AND HYPOTENSIVE PHARMACEUTICAL COMPOSITION CONTAINING SAME

[75] Inventors: Isao Yamatsu, Kawaguchi; Shinya Abe; Yuichi Inai, both of Tokyo; Toshiji Igarashi, Tokorozawa; Yoshikage Nakajima, Tokyo, all of Japan

[73] Assignee: Eisai Co., Ltd., Tokyo, Japan

[21] Appl. No.: 96,355

[22] Filed: Nov. 21, 1979

[30] Foreign Application Priority Data

Dec. 1, 1978 [JP] Japan .................. 53-147858

[51] Int. Cl.³ .................. A61K 31/045; C07C 29/136; C07C 33/02
[52] U.S. Cl. ................... 424/343; 568/875; 568/876; 568/884; 568/885
[58] Field of Search ............... 568/875, 876, 884, 885; 424/343

[56] References Cited

U.S. PATENT DOCUMENTS

| | | | |
|---|---|---|---|
| 3,304,333 | 2/1967 | Truscheit et al. | 568/884 |
| 3,449,407 | 6/1969 | Theimer et al. | 568/875 |
| 3,845,108 | 10/1974 | Roelofs et al. | 568/884 |
| 3,939,202 | 2/1976 | Matsui et al. | 568/875 |
| 3,953,532 | 4/1976 | Anderson et al. | 568/884 |
| 3,985,814 | 10/1976 | Doughtery | 568/876 |
| 4,198,532 | 4/1980 | Ochsner | 568/884 |

FOREIGN PATENT DOCUMENTS 2552365  5/1976  Fed. Rep. of Germany .

OTHER PUBLICATIONS

Rowland et al., JACS, vol. 78, pp. 4680-4683 (1956).
Yasumatsu et al., Agr. Biol. Chem., vol. 40, No. 9, pp. 1757-1763 (1976).

Primary Examiner—Natalie Trousof
Assistant Examiner—Vera C. Clarke
Attorney, Agent, or Firm—Blanchard, Flynn, Thiel, Boutell & Tanis

[57]  ABSTRACT

β, γ-Dihydropolyprenyl alcohols of the general formula:

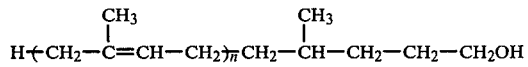

wherein n represents an integer of 8 to 10, exhibit hypotensive activity and anti-hepatic disease-activity.

11 Claims, 1 Drawing Figure

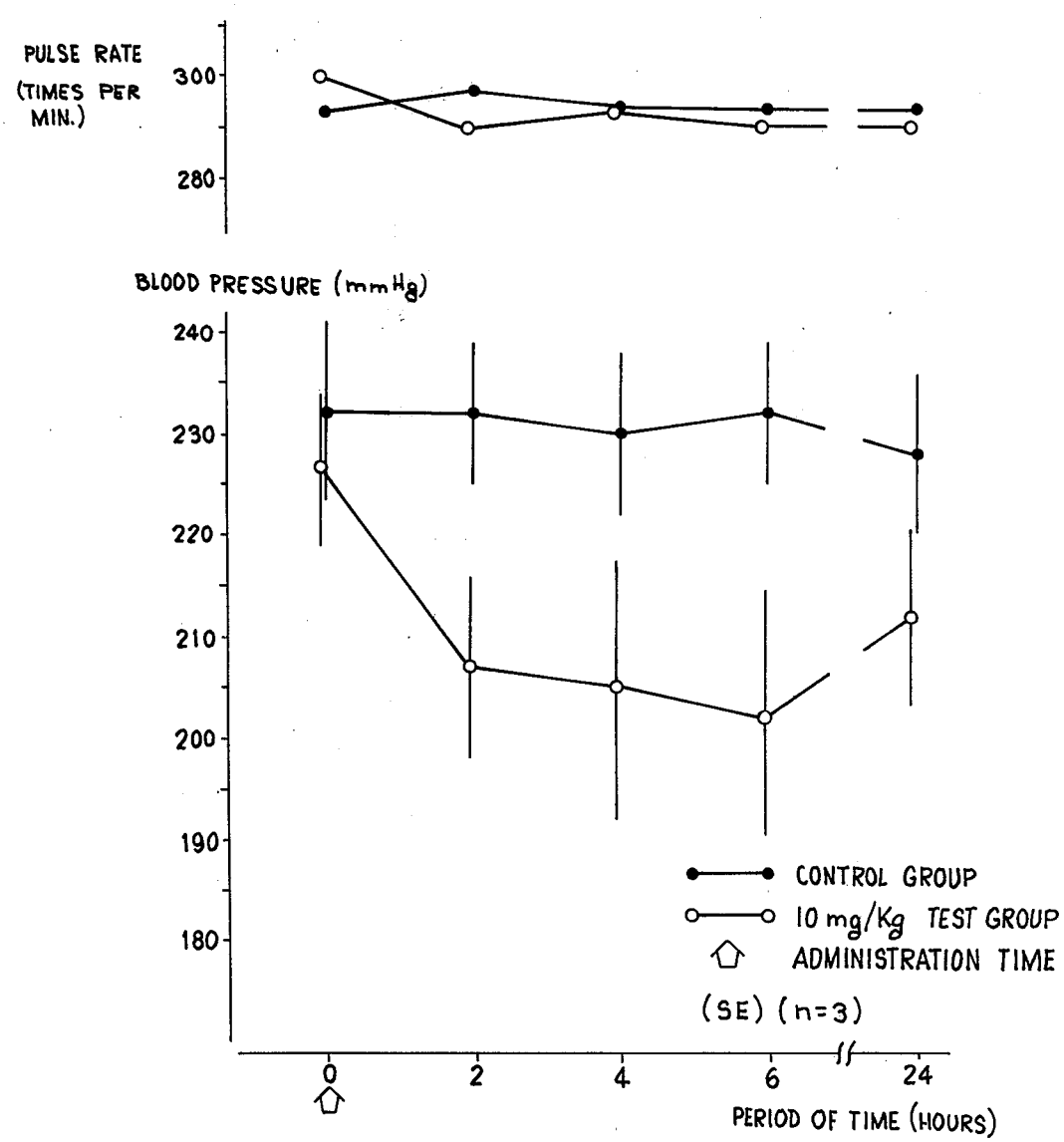

β, γ-DIHYDROPOLYPRENYL ALCOHOL AND HYPOTENSIVE PHARMACEUTICAL COMPOSITION CONTAINING SAME

The present invention relates to β, γ-dihydropolyprenyl alcohols of the general formula:

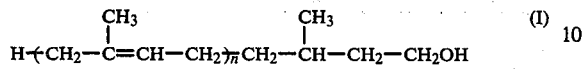

wherein n represents an integer of 8 to 10, and a pharmaceutical composition containing the same, useful for treating hypertension and hepatic disease.

Numerous hypotensive drugs have been developed for the treatment of hypertension. However, prior hypotensive drugs have various adverse side effects and, therefore, problems occur in the administration thereof, particularly when they are administered in large amounts or over a long period of time. For example, diuretic hypotensive drugs such as sulfonamide preparations and thiazide preparations have side effects of causing hyper-uricemia and hypo-potassemia; sympatholytic agents such as reserpine preparations and methyl dopa preparations have harmful side effects of causing thirst, clouding of consciousness and orthostatic hypotension; and vasodilator drugs such as apresoline have harmful side effects of causing headache, tachycardia and angina pectoris in many cases. After intensive investigations for the purpose of obtaining safer hypotensive drugs free of those defects, the inventors have discovered compounds of the above formula (I).

The compounds of the formula (I) of the present invention can be produced by a process comprising the following steps:

(a) reacting compounds of the general formula:

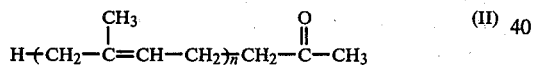

wherein n represents an integer of 8 to 10, with lower alkyl esters of cyanoacetic acid, in the presence of a base, to form compounds of the general formula:

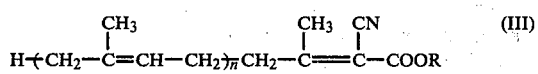

wherein n has the same meaning as set forth above and R represents a lower alkyl group;

(b) reducing the compounds of general formula (III) with a reducing agent, such as sodium borohydride, to obtain compounds of the general formula:

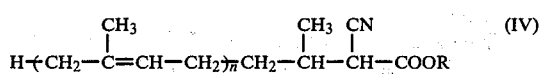

wherein n and R have the same meanings as set forth above;

(c) subjecting the compounds of general formula (IV) to decarboxylation in the presence of a strong alkali, such as potassium hydroxide, to obtain compounds of the general formula:

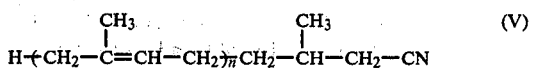

wherein n has the same meaning as set forth above;

(d) hydrolyzing the compounds of general formula (V) in the presence of a strong alkali, such as potassium hydroxide, to obtain compounds of the general formula:

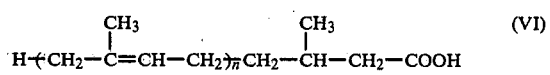

wherein n has the same meaning as set forth above; and (e) reducing the compounds of general formula (VI) with a reducing agent, such as sodium bis (2-methoxyethoxy) aluminum hydride or lithium aluminum hydride, to obtain compounds of the general formula:

wherein n has the same meaning as set forth above.

BRIEF DESCRIPTION OF THE DRAWING

The drawing is a graph showing the changes in the blood pressure and the heart rate of spontaneous hypertension rats (SHR) to which 3, 7, 11, 15, 19, 23, 27, 31, 35, 39-decamethyl-6, 10, 14, 18, 22, 26, 30, 34, 38-tetracontanonaene-1-ol of the present invention was administered.

The pharmacological effects and toxicities (acuate toxicities) of the compounds of the present invention, examined by animal tests, are described below.

Pharmacological tests

I. The hypotensive effect of the formula (I) compound, according to the invention, on spontaneously hypertensive rats (hereinafter referred to as SHR) of Okamoto and Aoki:

Method

The hypotensive effects of the test compounds on SHR of Okamoto and Aoki of about 35 weeks age were determined. The systolic blood pressure of the SHR was around 230 mmHg.

The test compounds were given to the SHR orally in the form of a suspension in aqueous acacia solution. The SHR were divided into a test compound group to which a test compound was administered and a control group to which only an aqueous acacia solution (free of test compound) was administered. Each group comprised three SHR.

The blood pressure of the SHR was measured with a Shimazu continuous tonometer SCS-301 (a product of Shimazu Seisakusho Co., Ltd.). Tail artery pressure was indirectly measured by a tail-cuff method.

The blood pressure was measured immediately before the administration and at 2, 4, 6 and 24 hours after the administration to determine the change in blood pressure with the passing of time.

The heart rate was determined by recording the pulse rate at the tail of the SHR with a tachometer of said tonometer SOS-301. Test Compound and Dose Test Compound 3, 7, 11, 15, 19, 23, 27, 31, 35, 39-Decamethyl-6, 10, 14, 18, 22, 26, 30, 34, 38-tetracontanonaene-1-ol Dose 10 mg/kg (body weight of SHR)

Results

The changes in the blood pressure and the heart rate due to the administration of the test compound are shown in the drawing.

It is evident from the drawing that in the control group, the blood pressure before the administration was 232±9 mgHg and it was 232±7 mmHg 6 hours after the administration, the blood pressure thus being substantially unchanged. In the group to which 10 mg/kg of the test compound was given, the blood pressure before the administration was 227±7 mmHg and it lowered to 207±9 mmHg two hours after the administration, further to 202±12 mmHg six hours after the administration and the blood pressure was 212±9 mmHg 24 hours after the administration. Thus, it was recognized that the test compound has a clear, long-lasting hypotensive effect. No effect on the heart rate was observed.

II. The effects of the formula (I) compound, according to the invention, on hepatic disease (hepatitis), induced by intraabdominal administration of D-galactosamine.

SD rats weighing about 250 g were used as test animals. D-Galactosamine hydrochloride (250 mg/kg each administration) and the test compound (50 mg/kg each administration) were administered intraabdominally to the rats on the schedule of experiments set forth below. After completion of the administration, blood was drawn from the test animals. The GPT value and alkali phosphatase value of the blood, which are indexes of the hepatic disease, were determined.

The test compound was used in the form of a suspension in 5% aqueous acacia solution. D-Galactosamine hydrochloride was used in the form of an aqueous solution thereof in distilled water, which solution was adjusted to pH 7 with potassium hydroxide. The rats were divided into three groups, i.e., a test compound group (comprising 9 rats) to which the test compound was administered, a control group (comprising 14 rats) to which 5% aqueous acacia solution free of the test compound was administered and a normal group (comprising 9 rats) to which neither the test compound nor D-galactosamine hydrochloride was administered.

Schedule of experiments

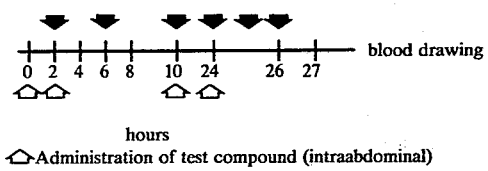

hours
△ Administration of test compound (intraabdominal)
▼ Administration of D-galactosamine (intraabdominal)

Test compound 3, 7, 11, 15, 19, 23, 27, 31, 35, 39-Decamethyl-6, 10, 14, 18, 22, 26, 30, 34, 38-tetracontanonaene-1-ol:

TABLE 1

| Test groups | Test Results | |
|---|---|---|
| | GPT Value (Carmen unit) | Alkali phosphatase value (KA-U) |
| Normal group | 46.5 ± 4.9 | 32.3 ± 2.5 |
| Control group | 1041.4 ± 200.8 | 70.9 ± 3.9 |
| Test compound group | 523.3 ± 111.7 | 63.7 ± 4.3 |

It is evident from the above table that the group of rats to which the test compound was administered (test compound group) had GPT values and alkali phosphatase values lower than those of the control group and closer to those of the normal group. This fact indicates that hepatic disease induced by the administration of D-galactosamine hydrochloride was ameliorated or prevented by the administration of the compound of the present invention.

Toxicity test 1,000 mg/kg of said test compound was administered orally to SD rats (males and females; about 200 g body weight). Neither death nor toxic side effects were observed.

It is apparent from the results of the above pharmacological tests and the toxical tests that the compounds of formula (I) of the present invention have an excellent effect of lowering the blood pressure and ameliorating hepatic disease induced by administration of D-galactosamine hydrochloride. They are substantially free of toxicity and, therefore, they are quite safe. Thus, the compounds of the formula (I) of the present invention are effective for the prevention and treatment of renal hypertension, endocrine hypertension, cardiovascular hypertension, neuropahtic hypertension and essential hypertension and they are effective for treating hepatic disease. The administration route and dose of the compounds of the formula (I) of the present invention can be selected and controlled suitably depending on the severity of the symptoms to be treated. For oral administration, the dose is 10–200 mg/day, preferably 50–100 mg/day, for adult human beings.

The compounds of the formula (I) of the present invention can be incorporated with conventional, pharmacologically acceptable carriers to prepare unit dosage forms in the form of powders, granules, tablets, capsules and injections by conventional techniques.

The following examples further illustrate the present invention.

EXAMPLE 1

Preparation of 3, 7, 11, 15, 19, 23, 27, 31, 35, 39-decamethyl-6, 10, 14, 18, 22, 26, 30, 34, 38-tetracontanonaene-1-ol:

(a) Preparation of ethyl 2-cyano-3, 7, 11, 15, 19, 23, 27, 31, 35, 39-decamethyl-2, 6, 10, 14, 18, 22, 26, 30, 34, 38-tetracontadecanoate:

35 Grams of nonaprenylacetone (formula II), 9.4 g of ethyl cyanoacetate, 5 g of ammonium acetate and 4 ml of acetic acid were dissolved in 300 ml of benzene. The azeotropic water was removed under reflux of benzene. After refluxing for 5 hours, 500 ml of hexane were added thereto. The mixture was washed with water and concentrated. The concentrate was purified by silica gel column chromatography with hexane-benzene solvent mixture as developer to obtain 30 g of the intended product as a white waxy substance.

Elementary analysis as $C_{53}H_{83}O_2N$:

|  | C | H | N |
| --- | --- | --- | --- |
| Theoretical (%): | 83.08 | 10.92 | 1.83 |
| Found (%): | 83.05 | 10.89 | 1.85 |

Mass spectrum: 765 (M+).

Infrared absorption spectrum ($cm^{-1}$): 2950, 2860, 2240, 1735, 1665, 1610, 1455, 1390, 1238, 1100.

Nuclear magnetic resonance spectrum ($CDCl_3$, ppm): 1.32(t, 3H), 1.60(S, 30H), 1.62(s, 3H), 1.98 (m, 34H), 2.25(m, 2H), 4.25(q, 2H), 5.10(m, 9H).

(b) Preparation of ethyl 2-cyano-3, 7, 11, 15, 19, 23, 27, 31, 35, 39-decamethyl-6, 10, 14, 18, 22, 26, 30, 34, 38-tetracontanonaenoate:

1.3 Grams of sodium borohydride were dissolved in 50 ml of ethanol. The resulting solution was added dropwise to a 15% solution of 25 g of the compound obtained in the above step (a) in dioxane under cooling with ice. After stirring for one hour, 10 ml of saturated aqueous ammonium chloride solution were added dropwise thereto and then 500 ml of n-hexane were added thereto. The organic layer thus separated was taken out, washed with water and then concentrated. The concentrate was purified by silica gel column chromatography with hexane/benzene solvent mixture as developer to obtain 21 g of the intended product as a white waxy substance.

Elementary analysis as $C_{53}H_{85}O_2N$:

|  | C | H | N |
| --- | --- | --- | --- |
| Theoretical (%): | 82.86 | 11.15 | 1.82 |
| Found (%): | 82.83 | 11.14 | 1.86 |

Mass spectrum: 767 (M+).

Infrared absorption spectrum ($cm^{-1}$): 2930, 2860, 2260, 1750, 1665, 1450, 1385, 1255, 1195.

Nuclear magnetic resonance spectrum ($CCl_4$, ppm): 1.15(t, 3H), 1.18(d, 3H), 1.40(m, 2H), 1.60(x, 27H), 1.68(s, 3H), 1.99(m, 34H), 2.13(m, 1H), 3.65(m, 1H), 4.25 (q, 2H), 5.10(m, 9H).

(c) Preparation of 1-cyano-3, 7, 11, 15, 19, 23, 27, 31, 35, 39-decamethyl-6, 10, 14, 18, 22, 26, 30, 34, 38-tetracontanonaene:

2.0 Grams of 85% potassium hydroxide and 13.5 g of the compound obtained in the above step (b) were dissolved in 100 ml of ethylene glycol. The mixture was refluxed under stirring for 24 hours. Then, the reaction mixture was poured into water, neutralized with dilute hydrochloric acid and extracted with hexane. The extract was washed with water and concentrated. The concentrate was purified by silica gel column chromatography with hexane/benzene solvent mixture as developer to obtain 8 g of the intended product as a white waxy substance.

Elementary analysis as $C_{50}H_{81}N$:

| Theoretical (%): | C | H | N |
| --- | --- | --- | --- |
| Theoretical (%): | 86.26 | 11.73 | 2.01 |
| Found (%): | 86.23 | 11.70 | 2.03 |

Mass spectrum: 695 (M+).

Infrared absorption spectrum ($cm^{-1}$): 2930, 2860, 2250, 1665, 1450, 1385, 1100.

Nuclear magnetic resonance spectrum ($CCl_4$, ppm): 1.05(d, 3H), 1.45(m, 2H), 1.60(s, 27H), 1.68(s, 3H), 2.00(m, 34H), 2.10(m, 1H), 2.25(d, 2H), 5.13(m, 9H).

(d) Preparation of 3, 7, 11, 15, 19, 23, 27, 31, 35, 39-Decamethyl-6, 10, 14, 18, 22, 26, 30, 34, 38-tetracontanonaenoic acid:

3.8 Grams of 85% potassium hydroxide and 8.0 g of the compound obtained in the above step (c) were dissolved in 100 ml of propylene glycol. The resulting solution was refluxed under stirring for 18 hours. Then, the reaction mixture was poured into water, neutralized with dilute hydrochloric acid and extracted with hexane. The extract was washed with water and concentrated. The concentrate was purified by silica gel column chromatography with hexane/benzene solvent mixture as developer to obtain 3.0 g of the intended product as a white waxy substance.

Elementary analysis as $C_{50}H_{82}O_2$:

|  | C | H |
| --- | --- | --- |
| Theoretical (%): | 83.97 | 11.56 |
| Found (%): | 83.96 | 11.56 |

Mass spectrum: 714 (M+).

Infrared absorption spectrum ($cm^{-1}$): 2500-3400, 2930, 2860, 1710, 1665, 1455, 1385, 1300, 1100.

Nuclear magnetic resonance spectrum ($CCl_4$, ppm): 1.00(d, 3H), 1.45(m, 2H), 1.64(s, 27H), 1.70(s, 3H), 2.00(m, 1H), 2.04(m, 34H), 2.24(d, 2H), 5.16 (m, 9H), 11.28(bs, 1H).

(e) Preparation of 3, 7, 11, 15, 19, 23, 27, 31, 35, 39-Decamethylene-6, 10, 14, 18, 22, 26, 30, 34, 38-tetracontanonaene-1-ol:

3.0 Grams of the compound obtained in the above step (d) were dissolved in 20 ml of benzene. 5.0 Grams of 70% solution of vitride in benzene were added dropwise thereto. After stirring for one hour, water was added to the mixture to decompose the excess sodium bis (2-methoxyethoxy)aluminium hydride.

The resulting precipitates were filtered out. 50 milliliters of acetone were added to the precipitates and the whole was refluxed and filtered. Acetone was distilled off from the filtrate. The resulting concentrate was combined with the former filtrate, washed with water and concentrated. The concentrate was purified by silica gel column chromatography with n-hexane/benzene solvent mixture as developer to obtain 1.6 g of the intended product as a white waxy substance.

Elementary analysis as $C_{50}H_{84}O$:

|  | C | H |
| --- | --- | --- |
| Theoretical (%): | 85.64 | 12.08 |
| Found (%): | 85.63 | 12.11 |

Mass spectrum: 700 (M+).

Infrared absorption spectrum ($cm^{-1}$): 3450, 2930, 2860, 1665, 1450, 1385, 1105, 1060.

Nuclear magnetic resonance spectrum ($CCl_4$, ppm): 0.95(d, 3H), 1.20(m, 1H), 1.23-1.55(m, 4H), 1.58(s, 27H), 1.66(s, 3H), 1.96(bs, 1H), 2.00 (m, 34H), 3.66(t, 2H), 5.15(m, 9H).

EXAMPLE 2

3, 7, 11, 15, 19, 23, 27, 31, 35-Nonamethyl-6, 10, 14, 18, 22, 26, 30, 34-hexatriacontaoctaene-1-ol:

The intended product in the form of a white waxy substance was prepared starting with octaprenylacetone in the same manner as described in Example 1.

Elementary analysis as $C_{45}H_{76}O$:

|  | C | H |
|---|---|---|
| Theoretical (%): | 85.37 | 12.10 |
| Found (%): | 85.38 | 12.10 |

Mass spectrum: 632 (M+).

Infrared absorption spectrum ($cm^{-1}$): 3450, 2930, 2860, 1665, 1450, 1385, 1105, 1060.

Nuclear magnetic resonance spectrum ($CCl_4$, ppm): 0.97 (d, 3H), 1.23 (m, 1H), 1.25-1.57 (m, 4H), 1.60 (s, 24H), 1.68 (s, 3H), 2.00 (bS, 1H), 2.03 (m, 30H), 3.68 (t, 2H), 5.17 (m, 8H).

EXAMPLE 3

3, 7, 11, 15, 19, 23, 27, 31, 35, 39, 43-Undecamethyl-6, 10, 14, 18, 22, 26, 30, 34, 38, 42-tetratetracontadecaene-1-ol:

The intended product in the form of a white waxy substance was prepared starting with decaprenylacetone in the same manner as described in Example 1.

Elementary analysis as $C_{55}H_{92}O$:

|  | C | H |
|---|---|---|
| Theoretical (%): | 85.87 | 12.05 |
| Found (%): | 85.86 | 12.03 |

Infrared absorption spectrum ($cm^{-1}$): 3450, 2930, 2860, 1665, 1450, 1385, 1105, 1060.

Nuclear magnetic resonance spectrum ($CCl_4$, ppm): 0.95 (d, 3H), 1.21 (m, 1H), 1.25-1.58 (m, 4H), 1.59 (s, 30H), 1.68 (s, 3H), 1.94 (bs, 1H), 2.01 (m, 38H), 3.68 (t, 2H), 5.16 (m, 10H).

EXAMPLE 4 CAPSULES

| Principal ingredient (Compound of Example 1) | 5 g |
|---|---|
| Microcrystalline cellulose | 80 |
| Corn starch | 20 |
| Lactose | 22 |
| Polyvinylpyrrolidone | 3 |
| Total | 130 g |

The above components were shaped into granules by a conventional method. The granules were charged in 1,000 gelatin hard capsules. Each capsule contained 5 mg of the principal ingredient.

EXAMPLE 5 POWDER

| Principal ingredient (Compound of Example 1) | 50 g |
|---|---|
| Microcrystalline cellulose | 400 |
| Corn starch | 550 |
| Total | 1,000 g |

The principal ingredient was dissolved in acetone. The solution was adsorbed on microcrystalline cellulose and then the whole was dried. The dry product was mixed with corn starch to obtain a powder by a conventional method. Thus, the powder containing the principal ingredient of 1/20 strength was obtained.

EXAMPLE 6 TABLETS

| Principal ingredient (Compound of Example 2) | 5 g |
|---|---|
| Corn starch | 10 |
| Lactose | 20 |
| Calcium carboxymethyl cellulose | 10 |
| Microcrystalline cellulose | 40 |
| Polyvinylpyrrolidone | 5 |
| Talc | 10 |
| Total | 100 g |

The principal ingredient was dissolved in acetone. The solution was adsorbed on microcrystalline cellulose and the whole was dried. The dry product was mixed with corn starch, lactose and calcium carboxymethyl cellulose. Then, an aqueous polyvinylpyrrolidone solution was added thereto as a binder. The mixture was shaped into granules by a conventional method. Talc as lubricant was then mixed therein and the mixture was shaped into tablets, each weighing 100 mg. Each tablet contained 5 mg of the principal ingredient.

EXAMPLE 7 INJECTION

| Principal ingredient (Compound of Example 3) | 10 g |
|---|---|
| Nikkol HCO-60 (a product of Nikko Chemical Co.) | 37 |
| Sesame oil | 2 |
| Sodium chloride | 9 |
| Propylene glycol | 40 |
| Phosphate buffer (0.1M, pH 6.0) | 100 ml |
| Distilled water | ad 1,000 ml |

The principal ingredient, Nikkol HCO-60, sesame oil and one-half of the propylene glycol were mixed together and heated to about 80° C. to obtain a solution. The solution was added with distilled water heated to about 80° C. in which the phosphate buffer, sodium chloride and the remainder of the propylene glycol had previously been dissolved to obtain 1,000 ml of the solution in total. The aqueous solution was poured in 2 ml ampoules. The ampoules were closed by fusion and then heated for sterilization.

Each ampoule contained 20 mg of the principal ingredient.

The embodiments of the invention in which an exclusive property or privilege is claimed are defined as follows:

1. A compound having the formula:

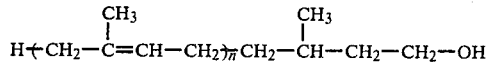

wherein n is an integer of 8 to 10.

2. A compound according to claim 1 wherein n is 8.
3. A compound according to claim 1 wherein n is 9.
4. A compound according to claim 1 wherein n is 10.
5. A pharmaceutical composition for treating hypertension and hepatic disease comprising a therapeutically effective amount of a compound as claimed in claim 1, in association with a pharmaceutically acceptable carrier, diluent or vehicle.
6. A pharmaceutical composition according to claim 5 wherein n is 9.

7. A method of treating hypertension which comprises administering to a hypertensive subject, a therapeutically effective amount of a pharmaceutical composition as claimed in claim 5.

8. A method of treating hepatic disease which comprises administering to a subject suffering from hepatic disease, a therapeutically effective amount of a pharmaceutical composition as claimed in claim 5.

9. A method which comprises:
(a) reacting a compound having the formula:

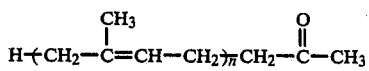

wherein n is an integer of 8 to 10, with a lower alkyl ester of cyanoacetic acid, in the presence of a base, to form a compound having the formula:

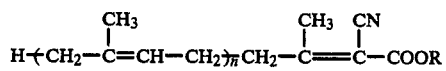

wherein n has the same meaning as set forth above and R is a lower alkyl group;
(b) reducing the compound obtained in step (a) with a reducing agent to obtain a compound having the formula:

wherein n and R have the same meanings as set forth above:
(c) subjecting the compound obtained in step (b) to decarboxylation in the presence of a strong alkali to obtain a compound having the formula:

wherein n has the same meaning as set forth above;
(d) hydrolyzing the compound obtained in step (c) in the presence of a strong alkali to obtain a compound having the formula:

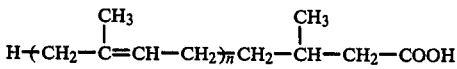

wherein n has the same meaning as set forth above; and
(e) reducing the compound obtained in step (d) with a reducing agent to obtain a compound having the formula:

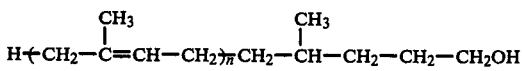

wherein n has the same meaning as set forth above.

10. A method as claimed in claim 9 in which said reducing agent is sodium bis(2-methoxyethoxy) aluminum hydride.

11. A method as claimed in claim 9 in which said reducing agent is lithium aluminum hydride.

* * * * *

UNITED STATES PATENT AND TRADEMARK OFFICE
CERTIFICATE OF CORRECTION

PATENT NO. : 4 325 974
DATED : April 20, 1982
INVENTOR(S) : Isao Yamatsu et al

It is certified that error appears in the above—identified patent and that said Letters Patent is hereby corrected as shown below:

Column 10, line 27; change the formula to read as follows:

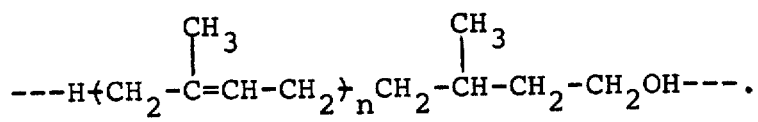

$$---H(CH_2-\underset{\underset{CH_3}{|}}{C}=CH-CH_2)_n CH_2-\underset{\underset{CH_3}{|}}{CH}-CH_2-CH_2OH---.$$

Signed and Sealed this

Seventh Day of September 1982

[SEAL]

Attest:

Attesting Officer

GERALD J. MOSSINGHOFF
Commissioner of Patents and Trademarks